US00PP31089P2

(12) United States Plant Patent
Hansen

(10) Patent No.: US PP31,089 P2
(45) Date of Patent: Nov. 19, 2019

(54) ***ANEMONE* PLANT NAMED 'SWEETLY'**

(50) Latin Name: *Anemone hupehensis*
Varietal Denomination: Sweetly

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 16/350,478

(22) Filed: Nov. 20, 2018

(51) Int. Cl.
*A01H 5/02* (2018.01)
*A01H 6/72* (2018.01)

(52) U.S. Cl.
USPC ..... Plt./263.1

(58) Field of Classification Search
USPC ..... Plt./263.1
See application file for complete search history.

*Primary Examiner* — Susan McCormick Ewoldt
*Assistant Examiner* — Karen M Redden

(57) ABSTRACT

The new and distinct cultivar of ornamental Japanese *Anemone* plant named *Anemone* 'Sweetly' with medium spreading habit, dense vertical peduncle of numerous semi-double flowers with deep rose-pink petals, beginning late summer and continuing into early fall, set just above the dark green, tri-foliate leaves with irregularly serrated to biserrated margins. The new plant is useful for landscaping as a specimen, en masse, or in containers.

1 Drawing Sheet

Latin botanical classification: *Anemone hupehensis*.
Variety denomination: 'Sweetly'.

STATEMENT REGARDING PRIOR DISCLOSURES UNDER 37 CFR 1.77(B)(6)

The first public disclosure of the claimed plant, in the form of a picture, was made by Walters Gardens, Inc. on Nov. 28, 2017 in their promotional calendar. No plants of *Anemone* 'Sweetly' have been sold as of the filing of this application anywhere in the world under any name. No disclosure of the new plant been made, more than one year prior the filing date of this application, and such disclosure within one year was either derived directly or indirectly from the inventor.

BACKGROUND OF THE INVENTION

The present invention relates to the new and distinct cultivar of Japanese *Anemone*, botanically known as *Anemone* 'Sweetly', and hereinafter referred to as the cultivar 'Sweetly' or the "new plant". The new plant was an intentional cross by the inventor at a wholesale perennial nursery in Zeeland, Mich., USA on Oct. 6, 2014 between 'Parnina' (not patented) as the female or seed parent and 'Pretty Lady Emily' U.S. Plant Pat. No. 22,303 as the male or pollen parent. The seeds were harvested and the new plant was assigned the breeder code 14-18-32 later in the evaluation process at the same nursery. *Anemone* 'Sweetly' has been asexually propagated through root cuttings first in 2016 at the same nursery in Zeeland, Mich. and subsequently also by sterile plant tissue culture. Plants of 'Sweetly' have been found to be stable and identical to the original selection in multiple generations of asexual propagation.

No plants of *Anemone* 'Sweetly' have been sold, in this country or anywhere in the world, prior to the filing of this application, nor has any disclosure of the new plant been made prior to the filing of this application with the exception of that which was disclosed within one year of the filing of this application and was either derived directly or indirectly from the inventor.

BRIEF SUMMARY OF THE PLANT

'Sweetly' is unique from all other Japanese *Anemone* known to the inventor. The new plant compares most closely with its male parent 'Pretty Lady Emily', 'Prince Henry' (not patented) and siblings 'Curtain Call Deep Rose' U.S. Plant Pat. No. 30,520 and 'Curtain Call Pink' U.S. Plant Pat. No. 30,739. Compared to 'Pretty Lady Emily' the new plant has more flowers per stem, the flowers have fewer petals per flower and the petal color is rosy mauve. The female parent 'Pamina' is taller in habit, has foliage that is more glossy than the new plant and the flower color is more pinkish and less rosy-pink. 'Curtain Call Pink' is smaller in habit and differs in flower color, the new plant having dark rosy pink petals. 'Curtain Call Deep Rose' is smaller in habit and has flowers that are more darker rose pink.

The new plant, *Anemone* 'Sweetly', is distinct from all other Japanese *Anemone* known to the inventor through the following combined characteristics:

1. Semi-double flowers of rich rose-pink on heavily branched panicle.
2. Flowering beginning late summer flowering and continuing into early fall.
3. Compact spreading habit and dark green foliage.

BRIEF DESCRIPTION OF THE DRAWINGS

The photographs of the new plant demonstrate the unique traits and the overall appearance of *Anemone* 'Sweetly'. The colors are as accurate as reasonably possible with color reproductions. Variation in ambient light spectrum, source and direction may cause the appearance of minor variation in color. The plant used in the photographs was two-years-old and was grown in a full-sun nursery trial garden in Zeeland, Mich. with supplemental water and fertilizer when needed. No pinching or plant growth regulators have been used.

DETAILED BOTANICAL DESCRIPTION

Figure 1:
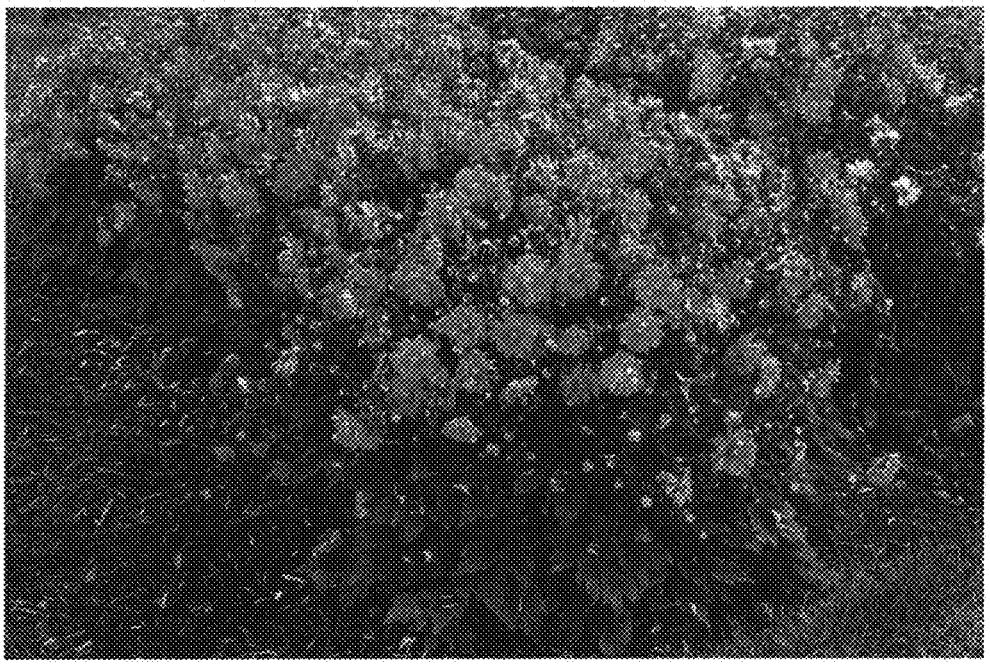
FIG. 1 shows the new plant in mid-season flowering habit.
Figure 2:
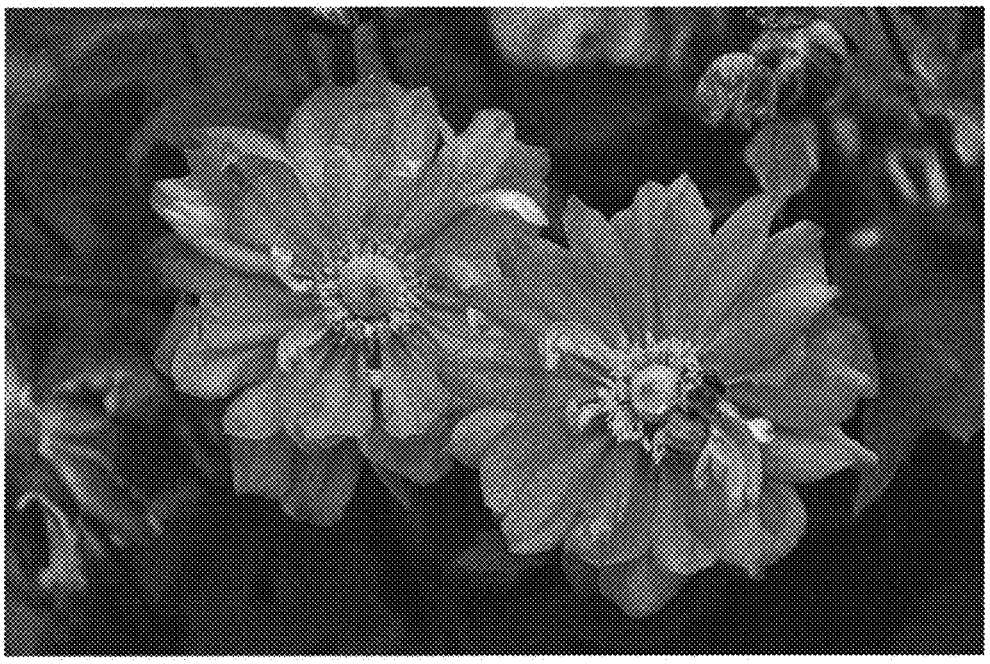
FIG. 2 shows a close-up of the flowers and buds.

The following descriptions and color references are based on the 2015 edition of The Royal Horticultural Society Colour Chart except where common dictionary terms are used. *Anemone* 'Sweetly' has not been observed under all possible environments. The phenotype may vary slightly with different growing environments such as temperature, light, fertility, soil pH, moisture and plant maturity levels, but without any change in the genotype. The following observations and size descriptions are based on three-year-old plants growing in a full-sun trial garden in Zeeland, Mich. Plants were given supplemental water and fertilizer but no plant growth regulators were used.

Botanical classification: *Anemone hupehensis;*

Parentage: Female or seed parent is 'Pamina'; male or pollen parent is 'Pretty Lady Emily';

Plant habit: Hardy herbaceous perennial; medium-sized; acaulescent mounded foliage with flowers arranged on heavily branched raceme just above foliage; foliage height to about 42.0 cm tall and flower height to about 58.0 cm tall; plant width about 80.0 cm at widest point at about 30 cm above soil level;

Growth rate: Moderately vigorous, finishing in a 65 mm plug from a rooted Stage 3 tissue culture explants in about 8 weeks and finishing in a 3.8 liter container from a 65 mm plug in about 8 weeks;

Root: Fine, fibrous; less than 0.5 mm diameter; heavily branched; color nearest RHS 165C;

Foliage: Basal, deltoid, tri-foliate, cleft to petiole; center lobe palmately ovate, with side lobes ovate to irregularly dissected; apex typically acute; base rounded; lobes frequently imbricate; margin irregularly serrate to bi-serrate; adaxial and abaxial surfaces glabrous; leaf attitude outwardly to slightly drooping; cauline leaves decreasing in size and with more acute apices;

Cauline leaves: Palmate to trifoliate; sessile; typically opposite pair subtending corymb branches; apex acute; base rounded; margin biserrate; to 10.0 cm long and 10.0 cm wide, decreasing distally; center lobe to 7.5 cm long and 3.5 cm wide, side lobes to 6.0 cm long and 4.5 cm wide;

Leaf size: To about 17.0 cm long and 14.5 cm across, center lobe to about 11.5 cm long and 6.5 cm across; side lobes average about 10.5 cm long and 6.5 cm across;

Leaf blade color: Cauline and basal — emerging adaxial between RHS 137B and RHS 137A, abaxial between RHS 147B and RHS 147C; cauline and basal — mature adaxial nearest RHS 139A, abaxial nearest RHS 147B;

Veins: Palmate; puberulent and slightly impressed on adaxial surface and slightly ridged and puberulent on abaxial surface;

Vein color: Adaxial nearest RHS 139A and abaxial nearest RHS 146D;

Petiole: Cylindrical; distally sulcate with single dorsal groove; sparsely micro-puberulent abaxial and adaxial, especially on young leaves; about 2.2 cm long and about 2.5 mm diameter at base; cauline leaves sessile;

Petiole color: Nearest RHS 146A;

Flower attitude: Mostly upright;

Inflorescence: Terminal corymb; with gynoecium surrounded by numerous androecium; average size flowering panicle about 25.0 cm across and about 25.0 cm tall; about 2 to 4 flowers per branched peduncle; with about 200 flowers per plant; flower timing in Michigan begins late summer and continues for about four weeks on the plant into early fall;

Buds about two days prior to anthesis and after sepals split; globose with rounded apex and rounded base; pubescent; about 12.0 mm diameter and about 13.0 mm tall;

Bud color: Nearest RHS N77A distally in high light regions and nearest RHS 146D toward base and in low light regions;

Petals: Lanceolate; with rounded to micro-apiculate apex, attenuate base; entire margin; glabrous adaxial; pubescent abaxial; irregularly sized, to 28.0 mm long and 12.0 mm wide near apex, average about 27.0 mm long and 10.0 mm wide near apex; about 24 petals per flower;

Petal color: Adaxial nearest RHS N66D; abaxial between RHS N74D;

Flower fragrance: None detected;

Flower persistence: Individual flowers lasting for about 7 days; self-cleaning;

Gynoecium: Numerous, between 200 and 320 per flower; in domed cap about 10.0 mm across;

*Style and stigma*.—Average 0.7 mm across and 0.7 mm long; color nearest RHS 145C.

*Ovary base*.—Globose, rounded apex; truncate base; 5.0 mm tall and 6.0 mm across in middle; color nearest RHS 145A.

Androecium: Numerous; about 120 per flower;

*Filaments*.—Fine; cylindrical; variable lengths between about 5.0 mm and 3.0 mm long and less than 0.1 mm diameter; color nearest RHS NN155B.

*Anther*.—Ellipsoidal; basifixed; longitudinal; rounded apex and base; about 2.0 mm long and 0.7 mm across; color nearest RHS 14B.

*Pollen*.—Abundant; color nearest RHS N25B.

Calyx: Ovate; strongly cupped; acute apex and base fused; margin entire; puberulent abaxial, glabrous adaxial; typically about 5 per flower; color abaxial nearest RHS N77A along margins and nearest RHS 146D near base and center regions; adaxial nearest RHS 71A along margins and between RHS N144D and RHS toward center and base;

Peduncle: About 60 per plant; cylindrical; pubescent; attitude vertical; to about 30 cm long and 4.0 mm diameter at base;

Peduncle color: Nearest RHS N186B;

Fruit and seed have not yet been observed;

Hardiness, pest and disease resistance: The new plant grows best with ample moisture, adequate drainage and full sun. Hardiness at least from USDA zone 5 zone 9. Disease and pest resistance beyond what is typical of that of other Japanese *Anemone* has not been observed.

I claim:

1. A new and distinct cultivar of ornamental Japanese *Anemone* plant named *Anemone* 'Fall in Love Sweetly', as herein described and illustrated.

* * * * *